United States Patent [19]

Csernátony et al.

[11] Patent Number: 5,514,132
[45] Date of Patent: May 7, 1996

[54] SPINAL OSTEOSYNTHESIS DEVICE

[75] Inventors: Zoltán Csernátony, Debrecen, Hungary; Jean-Francois Jeanson, Troyes, France

[73] Assignee: JBS S.A., Troyes, France

[21] Appl. No.: 302,888

[22] PCT Filed: Jan. 19, 1993

[86] PCT No.: PCT/FR93/00045

§ 371 Date: Sep. 19, 1994

§ 102(e) Date: Sep. 19, 1994

[87] PCT Pub. No.: WO94/16635

PCT Pub. Date: Aug. 4, 1994

[51] Int. Cl.⁶ .............................. A61B 17/70; A61B 17/68
[52] U.S. Cl. ................................................ 606/61; 606/60
[58] Field of Search .................... 606/61, 60, 73

[56] References Cited

U.S. PATENT DOCUMENTS

| | | |
|---|---|---|
| 4,257,409 | 3/1981 | Bacal et al. ............................... 606/61 |
| 4,409,968 | 10/1983 | Drummond . |
| 4,641,636 | 2/1987 | Cotrel ......................................... 606/61 |
| 4,738,251 | 4/1988 | Plaza . |
| 4,773,402 | 9/1988 | Asher et al. . |
| 5,084,049 | 1/1992 | Asher et al. ................................ 606/60 |
| 5,133,716 | 7/1992 | Plaza ........................................ 606/61 |
| 5,147,360 | 9/1992 | Dobousset ................................. 606/61 |

FOREIGN PATENT DOCUMENTS

| | | | |
|---|---|---|---|
| 0446092 | 9/1991 | European Pat. Off. ................. 606/61 |
| 485739 | 12/1975 | U.S.S.R. . |

OTHER PUBLICATIONS

Derwent Publication, AN-76-H7053X, Dec. 1975, 1 page.

*Primary Examiner*—Stephen C. Pellegrino
*Assistant Examiner*—Scott B. Markow
*Attorney, Agent, or Firm*—Spencer & Frank

[57] ABSTRACT

A spinal osteosynthesis device includes a plurality of implants, each having a yoke and an anchoring arrangement carried by the yoke for securing the implant to a selected vertebra. The device further has a connecting bar crossing each yoke; and a plurality of clamps tightening the bar to each yoke. Each clamp has a clamp body; and a pair of generally parallel-oriented claws spaced from one another by a slot and extending from the clamp body. The claws partially surround the respective yoke. The clamp body carries a tightening arrangement for rocking the clamp body about the connecting bar to tilt the claws toward the connecting bar so that the yoke is clamped thereagainst.

14 Claims, 7 Drawing Sheets

SPINAL OSTEOSYNTHESIS DEVICE

BACKGROUND OF THE INVENTION

The present invention relates to a spinal osteosynthesis device for supporting, straightening and fixing the spine, comprising implants anchored on the vertebrae, at least one connecting bar for supporting said implants and removable elements for locking the implants onto the bars.

Surgical treatment of deformations and instabilities of the vertebral spine has been developed in the last three decades. This kind of surgery is unquestionably necessary in the case of some frequent diseases as for instance scoliosis. Several facts, however, have limited its development for a long time. Such facts are e.g. as follows:

- both the patients and the surgeons used to have a false conception of these diseases,
- the interpretation of the instabilities and deformations of the vertebral spine have not been correct,
- the knowledge of biomechanics has been insufficient,
- there were no surgical experiences in that field and the techniques of implantation were not developed.

The most important event in the field of the development of that kind of surgery was the commercial introduction of the so called Harrington devices which are slightly out of date in view of the important advance in the field of biomechanics of the prostheses and the fact that, recently, the spinal surgery of the above diseases consists of obtaining a postolateral arthrodesis (with the exception of several methods as e.g. ligament replacement or vertebral disc prostheses not very much developed so far).

SUMMARY OF THE INVENTION

An object of the present invention is therefore to provide an improvement in devices of the above-outlined type and to offer a solution for adjustment of the implants in spinal surgery as well as an inspiration for the detailed analysis of the formation and the character of the curvature scoliosis.

A further object of the invention is to eliminate the difficulties connected with the devices applied currently and to provide a device which is simple to produce as well as to implant, which can efficiently be corrected during implantation without the need of introducing the implants in the spinal channel and which enables the change of surgical orientation by correcting the deformations. The mobility of a part of the spine is sacrificed only to an extent which depends on the degree of the deformation. The device should also enable anchoring or fixing the implants within the costotransversal space, above the dorsal part in order to obtain an inclination, rotation, a forward pull or backward push with respect to the vertebrae as well as compression or distraction within the correct axis of the spine and anchoring within the proper upper and lower limits.

These objects and others to become apparent as the specification progresses, are accomplished by the invention, according to which, briefly stated, the spinal osteosynthesis device includes a plurality of implants, each having a yoke and an anchoring arrangement carried by the yoke for securing the implant to a selected vertebra. The device further has a connecting bar crossing each yoke; and a plurality of clamps tightening the bar to each yoke. Each clamp has a clamp body; and a pair of generally parallel-oriented claws spaced from one another by a slot and extending from the clamp body. The claws partially surround the respective yoke. The clamp body carries a tightening arrangement for rocking the clamp body about the connecting bar to tilt the claws toward the connecting bar so that the yoke is clamped thereagainst.

In order to achieve a proper straightening and support of the spine, the implants are provided with:

- hooks bent in the same sense,
- hooks bent in opposite directions, the left hook being directed upwardly and
- hooks bent in opposite directions, the right hook being directed upwardly.

The yokes connecting the hooks are embracing the curvature of the vertebrae and preventing rotation with respect to the bars by opposite flattenings (flat parts).

According to a preferred embodiment, the threaded bore with the adjusting screw for tilting the clamp is arranged backwardly at an angle of about 25° and at a certain distance from the vertical plane of the claws of the clamp.

In order to improve the locking effect between the yoke connecting the hooks or eyes of the implants and the bars, the base of the clamp is prolonged on the side of the threaded bore receiving the adjusting and fixing screw.

The advantage obtained by the present invention is first of all that the device—similarly to the orthodontics—enables supporting and provides for the necessary stimulation to the spine for the correction of its deformations without sacrificing the mobility thereof. At the same time, the device consists of elements which do not traumatize the patients and their implantation is more simple then that of the devices used before.

DESCRIPTION OF THE PREFERRED EMBODIMENTS

Figure 1:
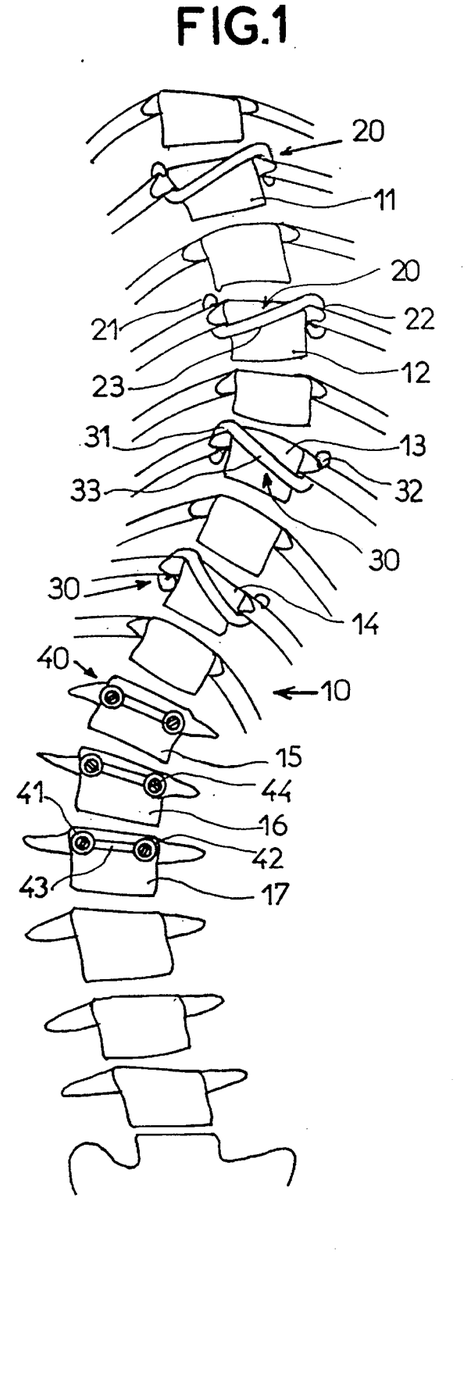
FIG. 1 is a rear view of a scoliotic spine provided with implants, but not yet straightened or supported.
Figure 2:
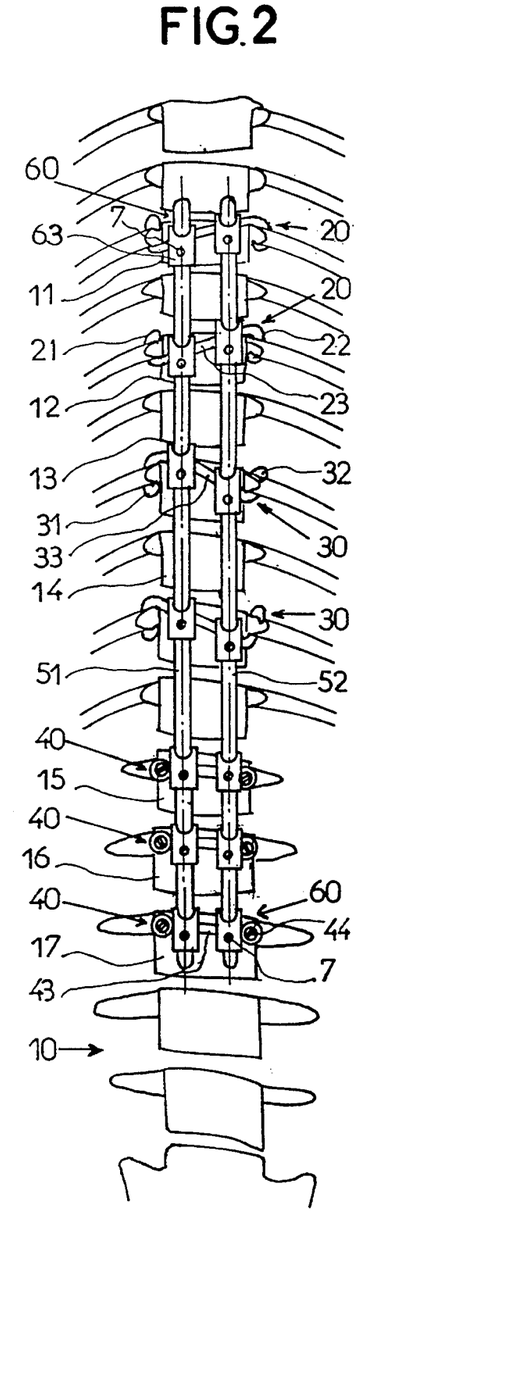
FIG. 2 is a view similar to FIG. 1 after straightening and supporting.
Figure 3A:
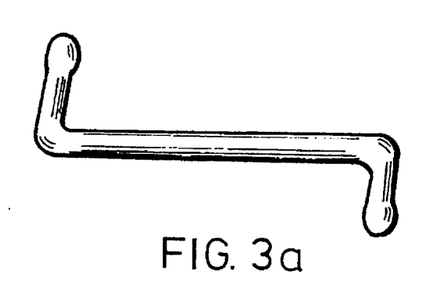
FIGS. 3a, 3b and 3c show a front view, a side view and a bottom view of an implant provided with hooks oriented in opposite directions.
Figure 3B:
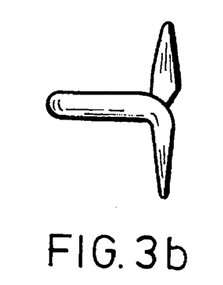
Figure 3C:
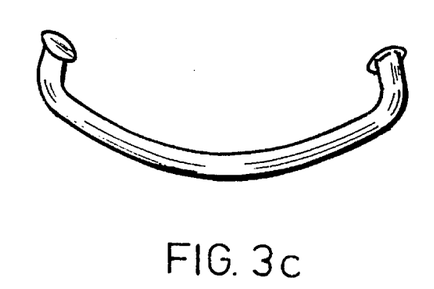
Figure 4A:
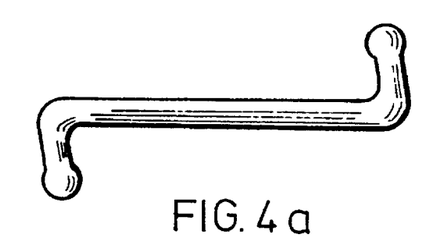
FIGS. 4a, 4b and 4c show a front view, a side view and a bottom view of another implant provided with hooks in opposite directions, wherein the right hook is directed upwardly.
Figure 4B:
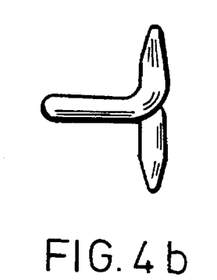
Figure 4C:
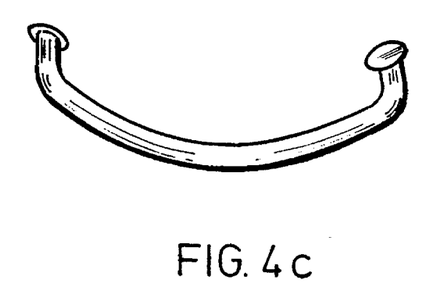
Figure 5A:
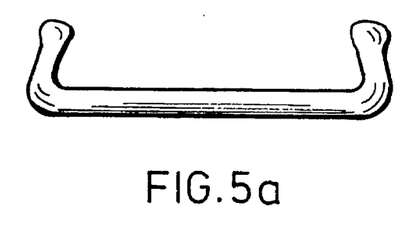
FIGS. 5a, 5b and 5c show a front view, side view and a bottom view of a further embodiment of the implant according to the invention provided with hooks directed in the same sense.
Figure 5B:
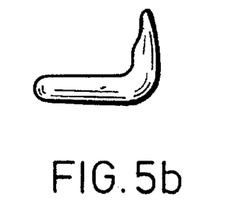
Figure 5C:
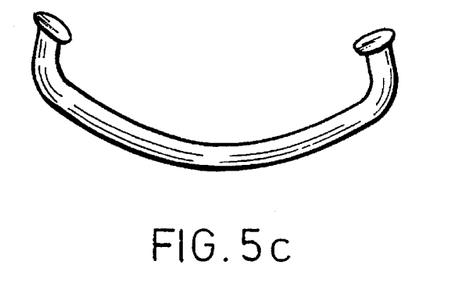
Figure 6A:
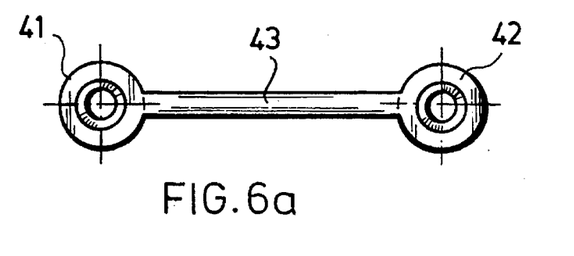
FIGS. 6a, 6b and 6c show a front view, a side view and a bottom view of an implant provided with eyes.
Figure 6B:
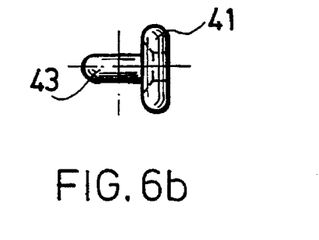
Figure 6C:
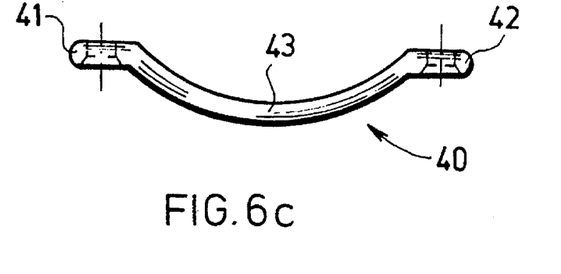
Figures 7A, 7B:
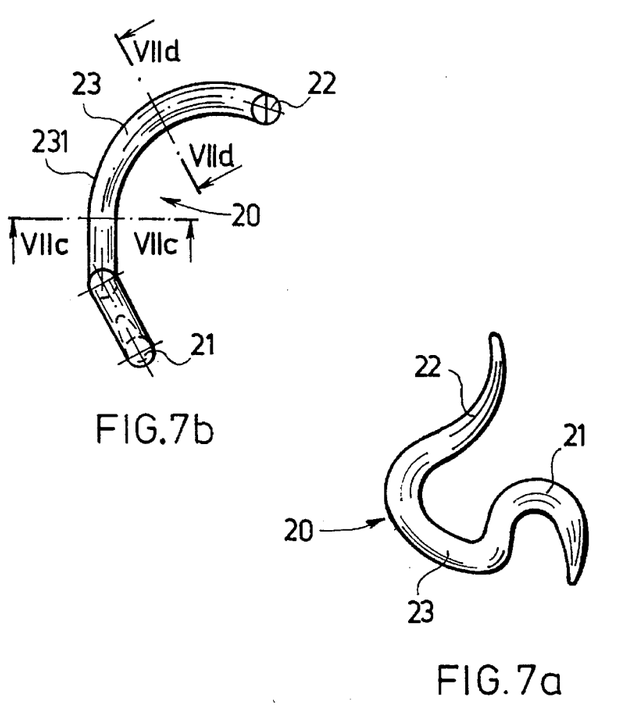
FIGS. 7a, 7b, 7c and 7d show a perspective view, a bottom view, and a side view along the line VIIC—VIIC and another side view along the line VIId—VIId of an implant provided with hooks of opposite directions, wherein the left hook is directed upwardly.
Figure 7C:
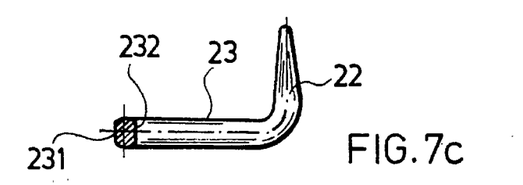
Figure 7D:
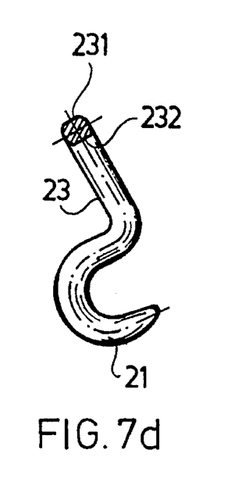
Figures 8A, 8B, 8D:
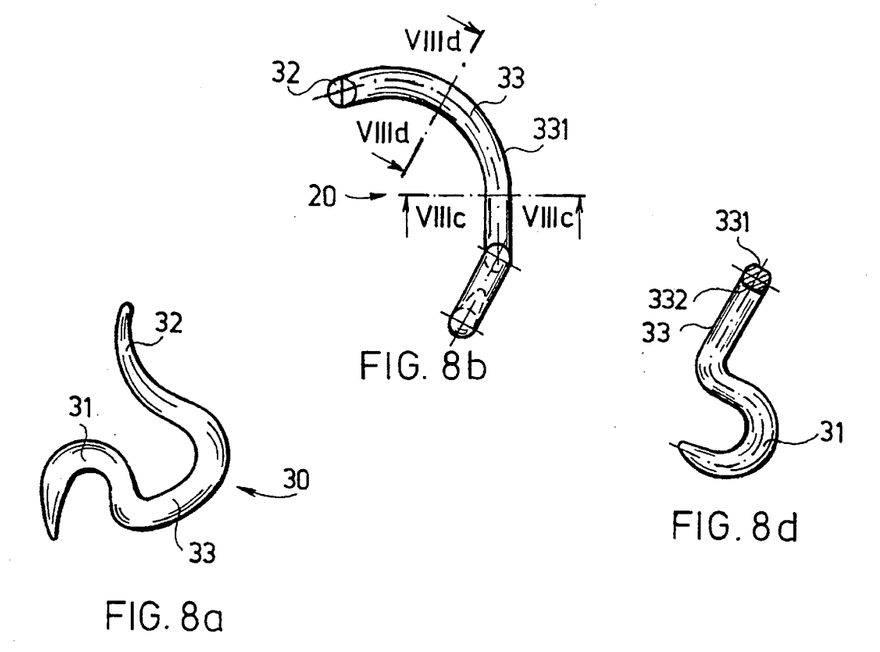
FIGS. 8a, 8b, 8c and 8d show a perspective view, a bottom view, and a side view along the line VIIIC—VIIIC and another side view along the line VIIId—VIIId of another implant provided with hooks of opposite directions, wherein the right hook is directed upwardly.
Figure 8C:
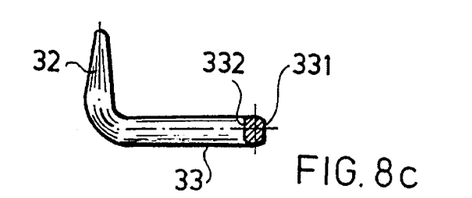

Vertebrae 11 to 17 of spine 10 shown in FIGS. 1 and 2 are provided with different implants. On vertebrae 11 and 12 there are implants 20 having hooks 21 and 22 connected with a yoke 23 provided with flat parts 231 and 232 (FIG. 9) wherein hook 21 on the left side is directed upwards. The vertebrae 13 and 14 have implants 30 with hooks 31 and 32 connected with a yoke 33 provided with flat parts 331 and 332 wherein the right hook 32 is directed upwardly. Lumbar vertebrae 15, 16 and 17 are provided with an implant 40 having eyes 41 and 42 connected by a yoke 43. Implant 40 is fixed by screws 44.

Figure 9:
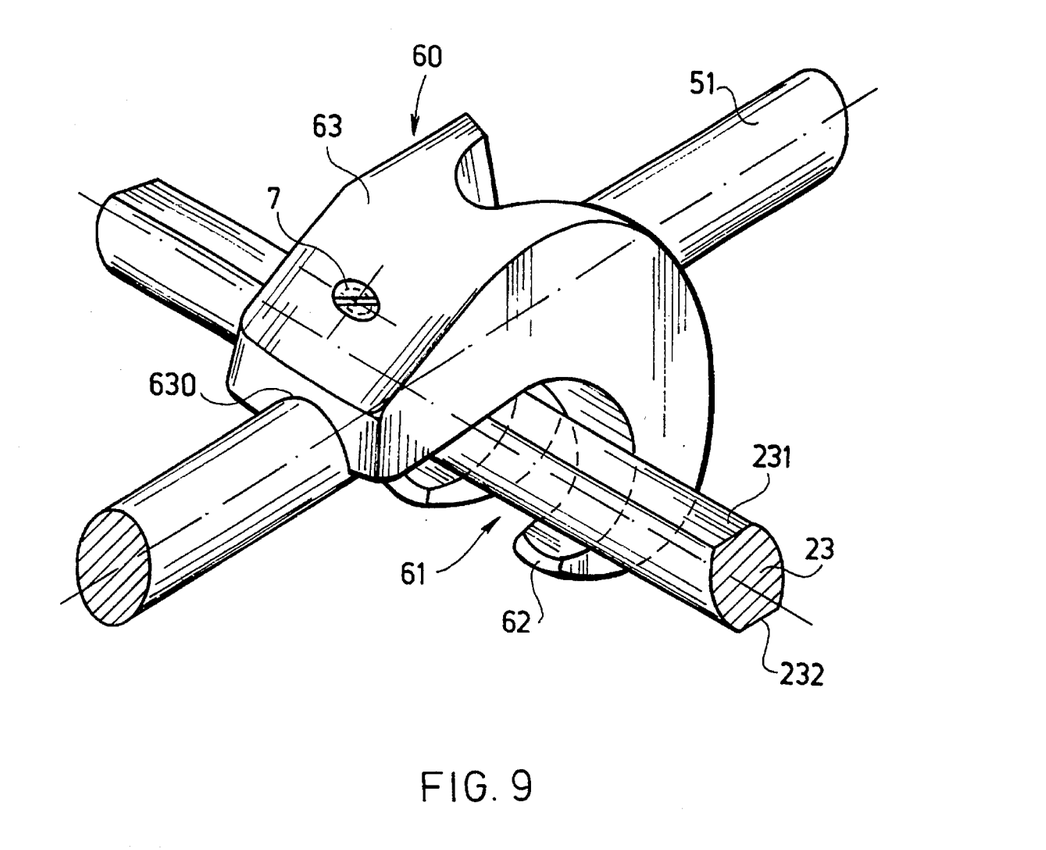
FIG. 9 shows a perspective view of a clamp tightening a bar and a yoke of an implant together.
Figure 10:
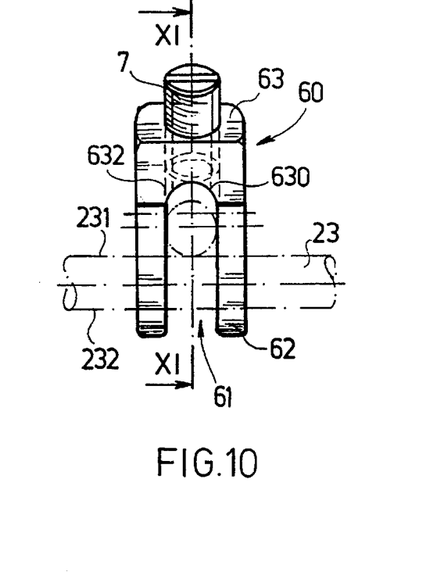
FIG. 10 is a front view of the clamp of FIG. 9 with the bar and yoke.

The straightened spine 10 can be seen in FIG. 2 wherein bars 51 and 52 are rigidly connecting yokes 23, 33 and 43 of implants 20, 30 and 40 by clamps 60 each provided with a slot 61 separating two claws 62 as best seen in FIGS. 9 and 10. The upper surface 63 of the clamp 60 is provided with a longitudinal semi-cylindrical groove 630 and a threaded bore 632 receives an adjusting screw 7 for producing a locking effect.

Examining now FIGS. 1 to 6c showing the elements of the device according to the invention, it should be noted that, in view of the numerous variations of the elements of the device, it is possible to obtain joints between the implants and the vertebrae which produce inclination, rotation, as well as a forward pull or backward push, depending always on the deformation of the spine 10. If necessary, compression or distraction within the proper axis of the spine and anchoring the upper and lower limits of the mounting can also be effected.

The implants provided with hooks are produced in two sizes which meet all the requirements and they may be provided, if needed, with bent yokes connecting the hooks of the implants. As seen in the Figures, in all the embodiments the hooks and the yoke of each implant constitutes a one-piece component.

The bent form of the implants showing concavity in the forward direction allows the bars 51 and 52 to be arranged on the front side (which is, however, not necessary). Such arrangements enable continuous bone healing without the need of fixing the implants on all levels. The connection between the implants and the bars is obtained by the clamps 60.

Referring to FIGS. 7a to 13 showing a practical embodiment of the invention, it should be noted that FIGS. 7a to 7d show an implant 20 with hooks 21 and 22 oriented in opposite directions, wherein the left hook 21 is directed upwardly. FIGS. 8a to 8d show an implant 30 with hooks 31 and 32 oriented in opposite directions wherein the right hook 32 is directed upwardly. In view of the particular form of the hooks 21, 22 and 31, 32, it is easy to insert first the upper hook 21, 32 on the right or left side, respectively and then to clamp the upper edge of the opposite side in the curvature of the other hook 22, 31.

It should also be noted that the flat parts 231, 232 and 331, 332 on the yokes 23, 33 allow to lock the implants in the supporting position until rigid connection is produced by bars 51, 52 which are tightened to the yokes of the implants by the clamps 60 as best seen in FIG. 9.

Figure 11:
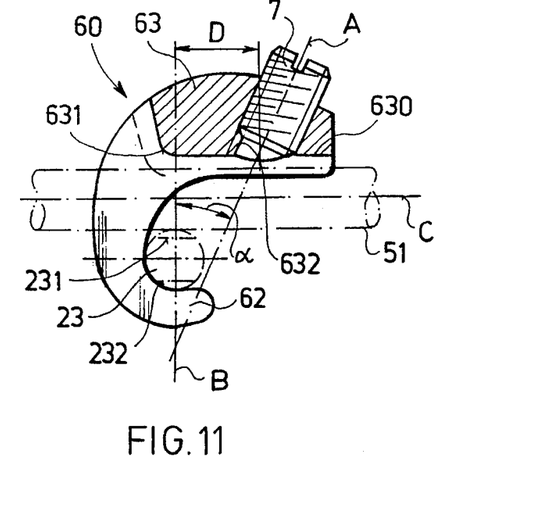
FIG. 11 is a section taken along line XI—XI of FIG. 10.
Figure 12:
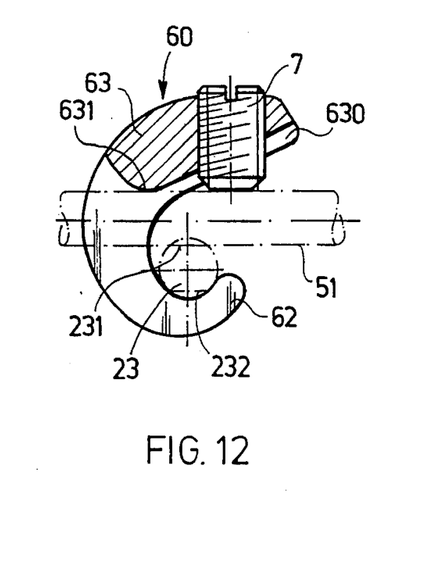
FIG. 12 is a view similar to FIG. 11, illustrating the clamp in a tightened state.
Figure 13:
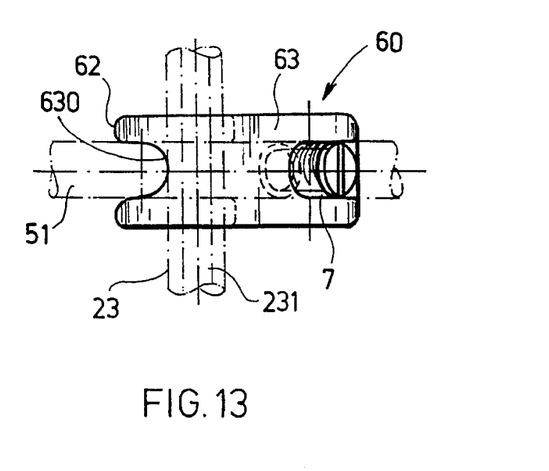
FIG. 13 is a top view of the clamp of FIG. 9 in a locked position.

FIGS. 9 to 13 show the mounting of the implants anchored to the vertebrae in the above outlined way. It is sufficient to contact all the implants with each of the bars 51, 52 and to hold the implants in their ideal position while being tightened to both bars 51, 52 by the clamps 60. The clamps 60 are placed first on the surface of the bars 51, 52 slightly above the yokes which are crossed by the bars 51, 52 so that the semi-cylindrical groove 630 in the body 63 of the clamp 60 is in contact with the surfaces of the bars 51, 52. Thereafter, clamps 60 are pushed against the yokes of the implants until these are embraced by the claws 62 of the clamps 60. The bars pass through the slot 61 of the respective clamp 60. Then, screw 7, threadedly held in bore 632, is advanced into the groove 630, and by virtue of its engagement with the associated bar 51 or 52 rocks counterclockwise (as viewed in FIGS. 11 and 12), as a result of which the claws 62 tilt and draw the implant yokes firmly against the respective bars 51, 52. The axis A of the bore 632 forms an angle of $\alpha$ of about 25° with a plane B extending perpendicularly to a longitudinal axis C of the groove 630. Due to this action the system fixes the implants against translation, rotation or tilting with respect to the bars 51, 52 and maintains an ideal position due to the flat parts 231, 232 and 331, 332 on the surfaces of the yokes. As seen in FIG. 11, the clamp 60 has an extension 633 in which the bore 632 is provided. The extension 633 increases the lever arm D between the axis A of the bore 632 and a rocking surface 631 on the clamp 60 about which the clamp 60 fulcrumates.

In this way, it is possible to minimize deformation of the system and, at the same time, to maintain the intentional straightening of the spine.

The three-dimensional effect produced by the device according to the invention enables both the correction of the three components of the scoliotic deformation and the restitution of sagittal curvatures, cyphosis and lordosis.

It will be understood that the above description of the present invention is susceptible to various modifications, changes and adaptations, and the same are intended to be comprehended within the meaning and range of equivalents of the appended claims.

We claim:

1. A spinal osteosynthesis device comprising
   (a) a plurality of spaced, one-piece implants for attachment to selected vertebrae of a spine in a series therealong; each said implant being composed of
      (1) a yoke having opposite ends; and
      (2) anchoring means carried by said yoke at the opposite ends for securing the implant to a selected vertebra;
   (b) a connecting bar crossing each yoke and arranged to extend along a spine; and
   (c) a plurality of clamps tightening said bar directly to each of said yokes; each of said clamp having
      (1) a clamp body;
      (2) a groove provided in said clamp body; said bar being received in said groove;
      (3) a pair of generally parallel-oriented claws spaced from one another by a slot and extending from said clamp body; said claws partially surrounding a respective said yoke; and
      (4) tightening means mounted in said clamp body for rocking said clamp body about said connecting bar to tilt said claws toward said connecting bar for clamping said yoke against said bar.

2. The spinal osteosynthesis device as defined in claim 1, wherein said groove is semi-cylindrical and further wherein said connecting bar and said groove have equal radii.

3. The spinal osteosynthesis device as defined in claim 1, wherein said tightening means comprises an adjusting screw threadedly received in a bore provided in said clamp body; said bore opening into said groove and said screw engaging said connecting bar.

4. The spinal osteosynthesis device as defined in claim 3, wherein said groove and said bore have respective longitudinal axes; further wherein the longitudinal axis of said bore forms an acute angle with a plane oriented perpendicularly to said longitudinal axis of said groove.

5. The spinal osteosynthesis device as defined in claim 4, wherein said angle is approximately 25°.

6. The spinal osteosynthesis device as defined in claim 1, wherein said bar passes through said slot.

7. The spinal osteosynthesis device as defined in claim 1, wherein said anchoring means of at least one of said implants comprises a hook formed as a bent portion at opposite ends of said yoke for hooking the implant about a vertebra.

8. The spinal osteosynthesis device as defined in claim 7, wherein said hooks of at least one of said implants extend in opposite directions from said yoke.

9. The spinal osteosynthesis device as defined in claim 7, wherein said hooks of at least one of said implants extend in the same direction from said yoke.

10. The spinal osteosynthesis device as defined in claim 1, wherein said yokes have opposite flat parts engaging said claws and said bar, respectively, for preventing rotation of said implants upon operating said tightening means of respective said clamps.

11. The spinal osteosynthesis device as defined in claim 1, wherein said tightening means comprises an adjusting screw threadedly received in a bore provided in said clamp body and having a bore axis; said bore merging into said groove and said screw engaging said connecting bar; said groove having an area of contact with said connecting bar forming a rocking location for said clamp, whereby said clamp tilts about said rocking location upon tightening of said adjusting screw to cause said claws to draw said yoke against said connecting bar; said rocking location being at a distance from said bore axis.

12. The spinal osteosynthesis device as defined in claim 11, wherein said clamp body has an extended part and further wherein said bore is situated in said extended part.

13. The spinal osteosynthesis device as defined in claim 1, wherein said anchoring means of at least a first one of said implants comprises a hook formed as a bent portion at opposite ends of said yoke for hooking the implant about a vertebra and further wherein said anchoring means of at least a second one of said implants comprises an eyelet formed at opposite ends of said yoke for securing the implant to a vertebra.

14. A spinal osteosynthesis device comprising (a) a plurality of spaced, one-piece implants, being composed of
  (1) a yoke having opposite ends; and
  (2) anchoring means carried by said yoke at the opposite ends for securing the implant to a selected vertebra;
(b) two connecting bars crossing each yoke and arranged to extend along a spine in a side-by-side relationship to one another; and
(c) a plurality of clamps tightening said bars directly to each of said yokes whereby each of said yokes coupling said two connecting bars to one another; each said clamp having
  (1) a clamp body;
  (2) a groove provided in said clamp body; a respective said bar being received in said groove;
  (3) a pair of generally parallel-oriented claws spaced from one another by a slot and extending from said clamp body; said claws partially surrounding a respective said yoke; and
  (4) tightening means mounted in said clamp body for rocking said clamp body about said respective connecting bar to tilt said claws toward said respective connecting bar for clamping each said yoke against said bars.

* * * * *